US00PP08018P

United States Patent [19]

Drewlow

[11] Patent Number: Plant 8,018

[45] Date of Patent: Oct. 27, 1992

[54] POINSETTIA PLANT NAMED WHITE YULETIDE

[75] Inventor: Lyndon W. Drewlow, Ashtabula, Ohio

[73] Assignee: Mikkelsens, Inc., Ashtabula, Ohio

[21] Appl. No.: 668,767

[22] Filed: Mar. 13, 1991

[51] Int. Cl.[5] ..... A01H 5/00
[52] U.S. Cl. ..... Plt./86.2
[58] Field of Search ..... Plt./86, 86.2

[56] References Cited

U.S. PATENT DOCUMENTS

Plt. 3,721 5/1975 Murison ..... Plt. 86

*Primary Examiner*—Howard J. Locker
*Attorney, Agent, or Firm*—Foley & Lardner

[57] ABSTRACT

A new Poinsettia plant named White Yuletide characterized by its white to light green bracts, excellent branching similar to White Rochford, relatively short and compact habit, tolerance to low light levels and high temperatures, excellent foliage retention, early flowering, cyathia which are non-splitting and very stress tolerant, and by its strong thick stems that provide a mounded display of bracts.

1 Drawing Sheet

The present invention comprises a new and distinctive cultivar of Poinsettia plant, botanically known as *Euphorbia pulcherrima,* and known by the cultivar name White Yuletide.

The creation of the new cultivar began in a controlled breeding program by crossing Mikkelsen Seedling No. 87-360-1 (seed parent) with Mikkelsen Seedling No. 87-261-3 (pollen parent). The seedling selection (identified as 88-426-2) was white in bract color and possessed inferior branching characteristics. The non-branching seedling was then grafted to the excellent branching type cultivar White Rochford (not patented) in an attempt to transfer the branching habit of White Rochford to the white seedling. The graft was successful, resulting in the new cultivar White Yuletide which has the branching habit of White Rochford while retaining all other desirable characteristics of the seedling.

Asexual reproduction of White Yuletide by stem cuttings as performed in Ashtabula, Ohio has shown that the unique features of this new Poinsettia are stabilized and are reproduced true to type in successive propagations.

The following characteristics in combination distinguish White Yuletide from White Rochford and other cultivated Poinsettia of this type known and used in the floriculture industry, including the commercially available cultivar V-14 White (U.S. Plant Pat. No. 4,938):

1. When five or more nodes are left after a pinch (apical tip removal), White Yuletide will develop full length shoots from each node like White Rochford and V-14 White, while the original seedling 88-426-2 will develop a full length shoot from only the upper three or four nodes, with the balance of shoots being somewhat repressed.
2. White Yuletide plants are 19 to 20 cm in length and are shorter than the 88-426-2 seedling (24 to 25 cm) when similar sized plants are left after pinching because there is little or no apical dominance in the branched types. Thus, all shoots develop to the same height instead of three or four shoots becoming dominant. White Rochford and V-14 White are taller at 29 to 30 cm than White Yuletide, as are taller growing branched cultivars.
3. White Yuletide has slightly lighter green leaves than the original seedling 88-426-2 and White Rochford, but the leaf color is similar to V-14 White. However, all would be classified as RHS 147A.
4. Bract coloration of White Yuletide and 88-426-2 is similar, being white with greenish tint ranging from RHS 155A white group to 157B green-white group, with V-14 White having more cream in bract (155A to 158D yellow-white group) and White Rochford being whiter (155A).
5. White Yuletide is more tolerant to the low light levels and high temperature conditions of the average home as it leaves do not yellow and drop like 88-426-2 and V-14 White under these conditions. While kept moist, White Yuletide is similar to the cultivar Mikkel Fantastic (U.S. Plant Pat. No. 3,721), both having excellent foliage retention.
6. White Yuletide has a cyathia (cluster of flowers in the center of the bract) intermediate in size between the small cyanthia of V-14 White and the larger cyathia of 88-426-2, with the cyathia of White Rochford being much larger.
7. White Yuletide is less susceptible to heat delay of flower bud initiation under night temperatures above 21° C. (like 88-426 in this respect) while both V-14 White and White Rochford are severely delayed at those temperatures. This is of great commercial importance, especially in the southern United States and when warmer than normal falls occur in the north.
8. Bract size of White Yuletide is similar to V-14 White at 25 to 30 cm, but larger than White Rochford at 20 to 25 cm. White Yuletide has a dense appearing bract like V-14 White as cyathia do not split apart like White Rochford. Bracts are more oblong in shape than V-14 White and White Rochford.
9. All other characteristics of White Yuletide are similar to the original seedling, for example, early flower initiation under natural short days, similar shaped leaves and bracts, retention of cyathia under stress conditions, and cyathia that do not split.

The accompanying colored photograph illustrates in top perspective view the overall appearance of White Yuletide, with the colors as true as it is reasonably possible to obtain in a colored reproduction of this type. The photograph was taken on Dec. 17, 1990 under rigid fiberglass greenhouse covering on an overcast day in Ashtabula, Ohio.

The following is a detailed description of my new cultivar based on plants produced in Ashtabula, Ohio during the fall season of the year. Plants were grown in 5 inch pots and measurements were taken 15 weeks after rooted cuttings were planted. Height measurements were taken from the soil line of the container. The plants were grown at 64°-68° F. night temperatures under 3500-4000 foot candles of light, and with 300 ppm Nitrogen, 150 ppm Potassium and 300 ppm Phosphorous nutritional levels with trace elements added. Habit of growth, foliage coloration, leaf variegation, size of leaves and flower size will be greatly influenced by nutritional and environmental conditions. Color references are made to The Royal Horticultural Society Color Chart except where general terms of ordinary dictionary significance are used. One application of 1500 ppm Cycocel growth regulator was applied to White Yuletide and all comparisons.

Parentage: Controlled cross of female Mikkelsen Seedling 87-360-1 with male Mikkelsen Seedling No. 87-261-3. The seedling selection (non-branching) was then grafted to the excellent branching cultivar White Rochford to create White Yuletide which possesses excellent branching.

Propagation:

(A) *Type cutting.*—Stem, 5 to 6 cm long.

(B) *Time to root.*—14 days at 21° C. summer, 18 days at 21° C. winter.

(C) *Rooting habit.*—Abundant, fibrous roots.

Plant description: Habit of growth, foliage coloration and size of leaf will be greatly influenced by nutritional and environmental conditions, thus data that follows was taken from plants grown under the conditions stated above.

(A) *Form.*—Upright; when apical meristem is removed (pinching) leaving 5 or more nodes above the soil line of pot, generally all lateral shoots will emerge and develop.

(B) *Habit of growth.*—Strong, thick stems that hold the bracts up for good flower display. Bottom stems elongate faster than upper stems, but produce mounded display of bracts with none hidden. Growth is vigorous. Depending on scheduling system, plants may need an application of a chemical growth regulator such as Cycocel. Nodal connections of stem are strong enough to hold up bracts without breaking.

(C) *Foliage description.*—Leaves are alternate and borne on 6-7 cm long petioles that are yellow-green in color. (1) Size: Mature leaves are 11 to 12 cm long by 9 to 10 cm wide at broadest point. (2) Shape: Leaf shape is variable from ovate to hastate with an acute apex and rounded base. (3) Texture: Upper surface glabrous, lower surface glabrous and rugose because of protruding veins. (4) Margin: Entire with intermediate lobing. (5) Color: Young foliage, top side 146A, under side 146C; mature foliage, top side 147A, under side 147B. (6) No epinasty from low levels of ethylene when boxed for up to 4 days.

Flowering description: Cyathia.

(A) *Flowering habits.*—Earlier flowering than most commercial cultivars, apparently having a longer critical day length for flower initiation. Under controlled day length, development time is approximately 10 weeks. Flowers earlier (like Yuletide (U.S. Plant Pat. No. 7,316) and Pink Yuletide) than most commercial cultivars under natural day length in Ohio, but it takes approximately the same time to develop when tested under exact controlled day lengths with other commercial cultivars. Early flower initiation is of commercial significance. Involucre is almost flat with only slight reflexing.

(B) *Natural flowering season.*—November 15 to 25 under growing conditions in Ohio.

(C) *Cyathia description.*—Are very stress tolerant, remaining in the involucre for a considerable time under low fertility, low light and high temperature conditions; severe drying may cause them to drop.

(D) *Cyathia borne.*—Stay closely clustered for a considerable time without growing apart (splitting). Flowering can be initiated any time of the year by controlling day length; cyathia will continue to initiate until day length is greater than approximately 13 hours.

(E) *Quantity of cyathia.*—Is highly dependent on cultural practices and can vary from minimum of 8 to 10 to as many as 25 to 30; cyathia will continue to develop from November to April resulting in the large number.

(F) *Bracts.*—Last true leaves are white in color. (1) Shape: Ovate (first true bracts) to oblong (later formed bracts); first mature bracts are 13 to 14 cm long and 8.5 to 9.5 cm wide; petioles 30 cm long. (2) Color at maturity: 155A to 157B; young bract 158A; under side 155A. (3) Number of bracts: Up to 40 or more depending on growing conditions, with 20 to 25 normal number; bract size and number varies with growing conditions, for example, if plants are pinched and growth regulators are used.

(G) *Reproductive organs.*—(1) Stamens: Numerous. (a) Anther shape: Oblong, yellow in color. (b) Filament color: White. (c) Pollen color: Yellow. (2) Pistils: (a) Stigma shape: Forked, yellow-green in color. (b) Style color: Yellow-green. (c) Ovaries: 3 celled; 3 mm in size; yellow green when stigma receptive. (3) Nectar cups: Usually 1 and possibly 2 nectar cups on each cyathia; yellow in color; nectar readily available on maturing cyathia.

Disease resistance: During box test of four days no botrytis developed on bracts whereas other white cultivars developed botrytis. Bracts 30 days or older have shown no botrytis under greenhouse conditions.

Other important characteristics: The compact growth habit of White Yuletide can either eliminate growth regulators or cut their use to a minimum. This results in larger bracts as most growth regulators reduce bract size.

I claim:

1. A new and distinct cultivar of Poinsettia plant named White Yuletide, as illustrated and described.

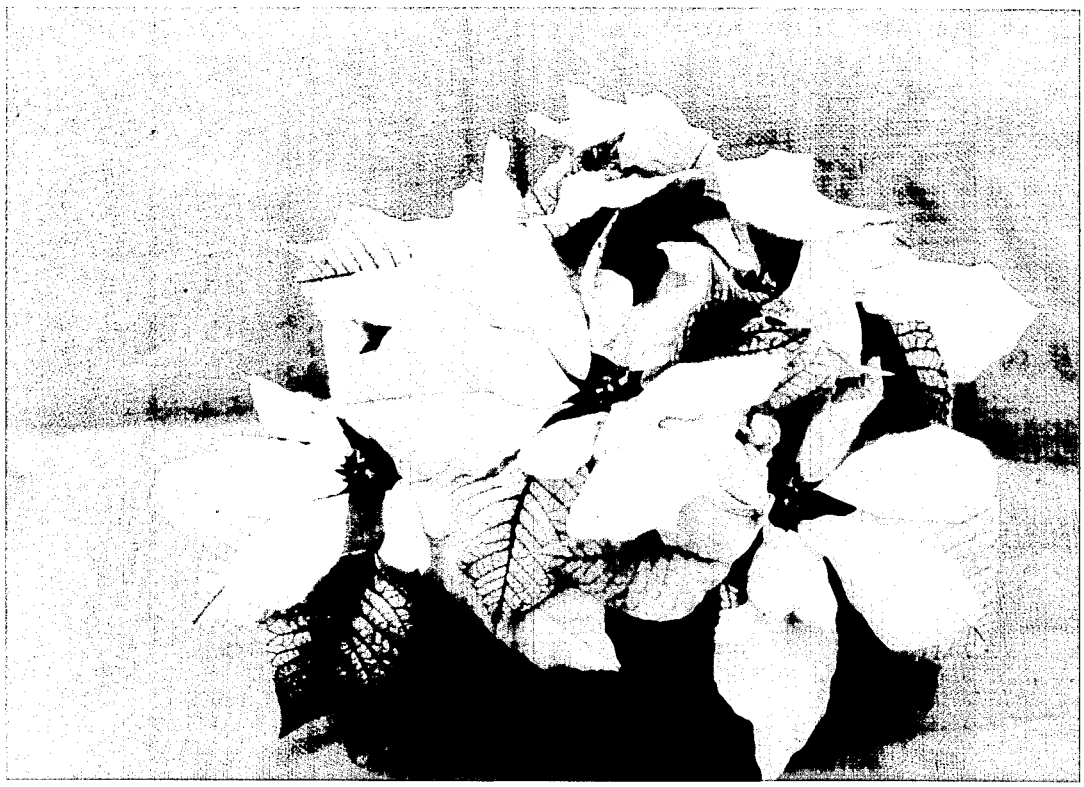

* * * * *